US008403958B2

(12) United States Patent
Schwab

(10) Patent No.: US 8,403,958 B2
(45) Date of Patent: Mar. 26, 2013

(54) SYSTEM AND METHOD FOR CORRECTING SPINAL DEFORMITY

(75) Inventor: Frank J. Schwab, New York, NY (US)

(73) Assignee: Warsaw Orthopedic, Inc., Warsaw, IN (US)

(*) Notice: Subject to any disclaimer, the term of this patent is extended or adjusted under 35 U.S.C. 154(b) by 1124 days.

(21) Appl. No.: 11/842,693

(22) Filed: Aug. 21, 2007

(65) Prior Publication Data

US 2008/0051788 A1 Feb. 28, 2008

Related U.S. Application Data

(60) Provisional application No. 60/839,028, filed on Aug. 21, 2006.

(51) Int. Cl.
A61B 17/70 (2006.01)

(52) U.S. Cl. ...................................................... 606/246

(58) Field of Classification Search .......... 606/246–279; 248/113, 58, 229.11, 229.13, 112, 110, 231.31, 248/231.9, 231.91, 111; 417/312; 411/401, 411/400; 24/134; A61B 17/70; E21F 17/02; A46B 17/02; A47B 96/06; A47K 1/08
See application file for complete search history.

(56) References Cited

U.S. PATENT DOCUMENTS

| 369,318 | A | * | 9/1887 | Craine | 248/113 |
|---|---|---|---|---|---|
| 1,563,817 | A | * | 12/1925 | Wright | 248/113 |
| 4,084,532 | A | * | 4/1978 | Feder | 114/218 |
| 4,798,298 | A | * | 1/1989 | Ursetta | 211/70.5 |
| 5,183,164 | A | * | 2/1993 | Heinzle | 211/70.5 |
| 6,105,915 | A | * | 8/2000 | Naman et al. | 248/309.1 |
| 6,811,567 | B2 | | 11/2004 | Reiley | |
| 7,344,537 | B1 | * | 3/2008 | Mueller | 606/278 |
| 2003/0004511 | A1 | * | 1/2003 | Ferree | 606/61 |

OTHER PUBLICATIONS

Scientific American, Apr. 1936, pp. 178-181, "Bone Surgery With Machine Tools", Fred H. Albee.*

* cited by examiner

Primary Examiner — Eduardo C Robert
Assistant Examiner — David Comstock

(57) ABSTRACT

An anchor for attaching an elongate flexible member to bone. The anchor includes a base adapted for attaching to bone and a connector mounted on the base. The connector includes a cam positioned for engaging the flexible member when the base is attached to bone. The cam is pivotable between an open position in which the flexible member may be moved relative to the connector and a closed position in which the cam engages the flexible member so the flexible member is fixed relative to the connector.

29 Claims, 11 Drawing Sheets

SYSTEM AND METHOD FOR CORRECTING SPINAL DEFORMITY

CROSS-REFERENCE TO RELATED APPLICATIONS

This application claims priority from U.S. Provisional Patent Application No. 60/839,028 filed Aug. 21, 2006, entitled, "TECHNIQUES AND ENSEMBLE OF DEVICES FOR SPINAL SURGERY WITH FLEXIBLE LINKAGE ELEMENTS, ATTACHMENT SYSTEMS AND ANCHORAGE MEMBERS," which is hereby incorporated by reference.

BACKGROUND

This invention generally relates to a system and methods for correcting or treating spinal deformities and other conditions through a non-fusion procedure.

A variety of systems and devices are available to correct or stabilize a spinal column. Some of these systems include anchors adapted to attach to vertebrae and linking elements such as rods and plates that rigidly attach to the anchors to rigidly fasten several vertebrae together to promote the vertebrae to fuse together. Bone material may be added to further promote fusion of the vertebrae. Other systems have been devised that do not promote fusion. If fusion is not desired, but correction of deformity or stabilization of spinal elements is desired, then continued movement between vertebrae is desired. Some systems that resist fusion link vertebrae with flexible tethers, flexible rods, or other flexible linkage elements, allowing the vertebrae to move relative to each other. Current systems designed for attaching flexible linkage elements are primarily based on concepts and designs used for rigid rods. Some of the systems allow loading to be applied to the vertebrae to provide a corrective force. These systems remain bulky and do not specifically capitalize on the properties of the flexible linkage members. Thus, there is a need for surgical procedures and systems adapted to attach linkage members to vertebral or other bone anchors but which overcome the shortcomings of prior procedures and systems.

BRIEF SUMMARY

The present invention relates to an anchor for attaching an elongate flexible member to bone. The anchor comprises a base adapted for attaching to bone and a connector mounted on the base. The connector includes a cam positioned for engaging the flexible member when the base is attached to bone. The cam is pivotable between an open position in which the flexible member may be moved relative to the connector and a closed position in which the cam engages the flexible member so the flexible member is fixed relative to the connector.

In another aspect, the present invention relates to an anchor for attaching an elongate flexible member to bone. The anchor comprises a base adapted for attaching to bone and a connector mounted on the base. The connector includes a body having a tapered opening and a gripper slidably received in the tapered opening for engaging the flexible member. The gripper is slidable along the opening between an open position in which the flexible member may be moved relative to the connector and a closed position in which the gripper engages the flexible member so the flexible member is fixed relative to the connector.

In yet another aspect, the invention includes a system for changing alignment of vertebrae of a spinal column. The system comprises a plurality of elongate flexible members. Each of the members has a length sufficient to span at least one pair of vertebrae in the spinal column. Further, the system comprises a plurality of anchors. Each anchor includes a connector for connecting at least one of the plurality of elongate members to the anchor.

Still another aspect of the invention includes a method of changing alignment of vertebrae of a spinal column. The method comprises mounting a first anchor on a first vertebra and mounting a second anchor on a second vertebra. An elongate flexible member is connected to the first anchor and to the second anchor. The elongate member is tensioned without disconnecting the member from the first anchor or the second anchor.

In a further aspect, the invention includes a method of changing alignment of vertebrae of a spinal column. The method comprises mounting a first anchor on a first vertebra and mounting a second anchor on a second vertebra. An elongate flexible member is connected to the first anchor. The elongate member is tensioned and connected to the second anchor. Tension in the elongate member is adjusted after connecting the tensioned elongate member to the second anchor.

Still further, the invention includes a method of changing alignment of vertebrae of a spinal column. The method comprises screwing a first anchor into a pedicle of a first vertebra and screwing a second anchor into a pedicle of a second vertebra. An elongate flexible member is connected to the first anchor and to the second anchor.

Other aspects of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION

Figure 1:
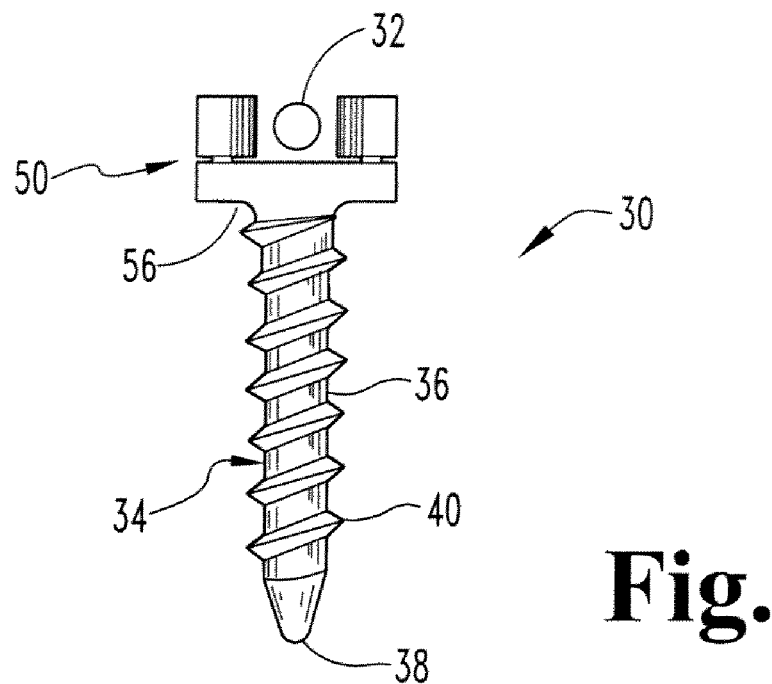
FIG. 1 is a side view of a first embodiment of an anchor of the present invention.

Referring now to the drawings and in particular FIG. 1, an anchor of one embodiment of the present invention is designated in its entirety by the reference number 30. The anchor 30 is intended to attach an elongate flexible member 32 to bone (e.g., a pedicle of a vertebra) as will be described in further detail below. As further shown in FIG. 1, the anchor 30 includes a base, generally designated by 34 for attaching the anchor to bone. The base 34 includes a longitudinal shaft 36 having a tip 38 at one end. In one embodiment, the tip 38 has a rounded point for entering bone without inadvertently damaging surrounding bone or tissue. A thread 40 extends along the shaft 36 thereby forming a screw for advancing the shaft into the bone and holding the shaft in place in the bone. A connector, generally designated by 50 is mounted on the base 34.

Figure 2:
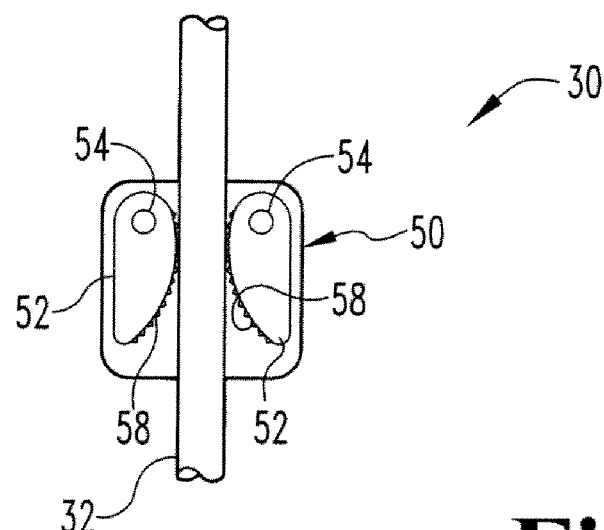
FIG. 2 is an end view of the anchor of the first embodiment showing an elongate member positioned between cams of the anchor.
Figure 3:
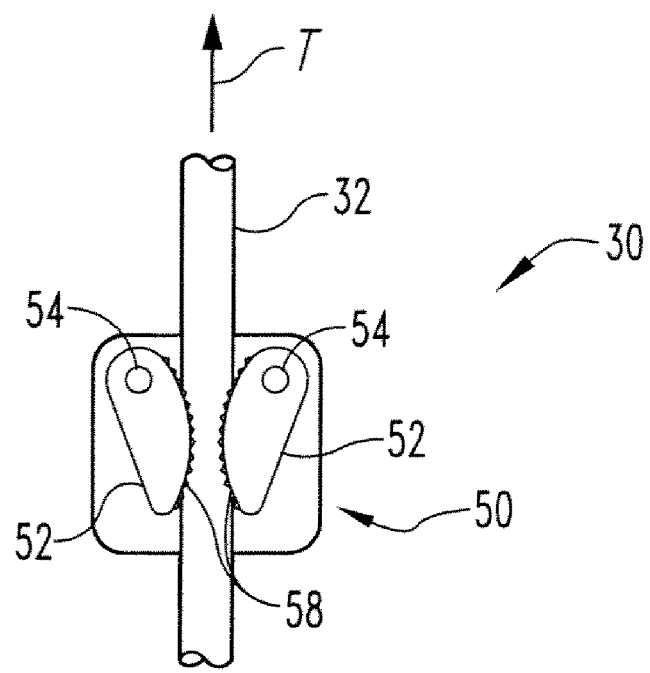
FIG. 3 is a view similar to FIG. 2 but showing the elongate member under tension so the cams compress the elongate member.

As illustrated in FIG. 2, the connector 50 includes one pair of cams 52 pivotally mounted on pins 54 attached to a head 56 (FIG. 1) of the base 34 at an end of the shaft opposite tip 38. The cams 52 include serrated surfaces 58 that face one another so they are positioned for engaging the flexible member 32 when the member is positioned between them. In an alternative embodiment (not shown), the facing surfaces are roughened using some other technique (e.g., knurling or grit blasting) to hold the flexible member 32. The cams 52 are pivotable between an open position as shown in FIG. 2 in which the flexible member 32 may be moved relative to the connector 50 and a closed position as shown in FIG. 3 in which the cams engage and compress the flexible member so the flexible member is fixed relative to the connector. In one embodiment, the cams 52 are biased toward the closed position so they tend to grasp the flexible member 32. As will be appreciated by those skilled in the art, the cams 52 of the connector 50 pivot to permit tension in the flexible member 32 to be increased and grip the member tighter when tension in the member is increased by pulling the member in the direction indicated by the arrow T in FIG. 3.

The system described above can be used to correct or treat spinal deformities and/or conditions using a procedure that does not promote vertebral fusion. The system includes one or more anchors that can be attached to one or more vertebrae or other bones. The anchors are linked to one another by a elongate flexible member. By applying tension to the elongate member, it is envisioned that deformity can be corrected and undesirable motions may be restrained.

Figure 4:
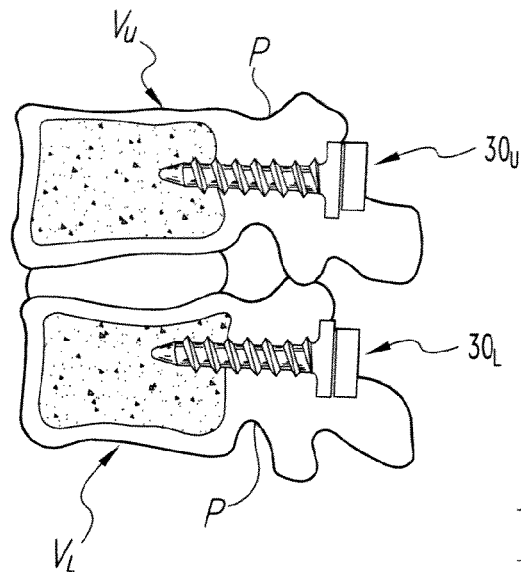
FIG. 4 is a left side elevation of the pair of adjacent vertebrae showing anchors of the first embodiment attached.
Figure 5:
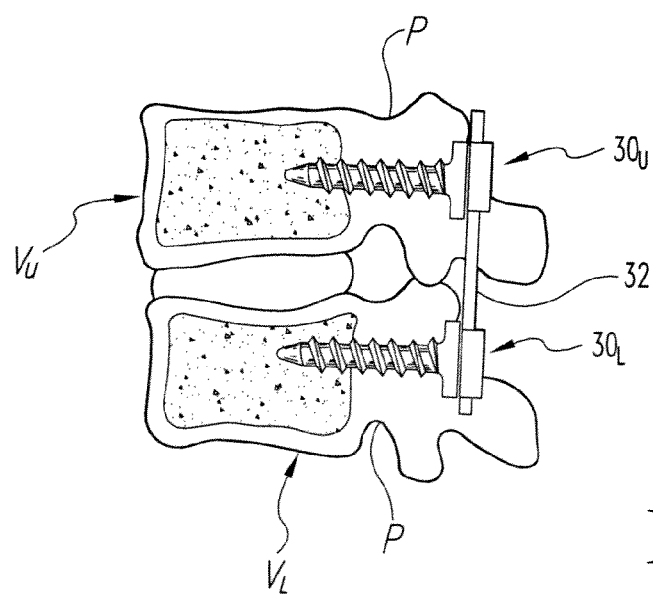
FIG. 5 is a left side elevation of the vertebrae and anchors of FIG. 4 with elongate members connected to the anchors.
Figure 6:
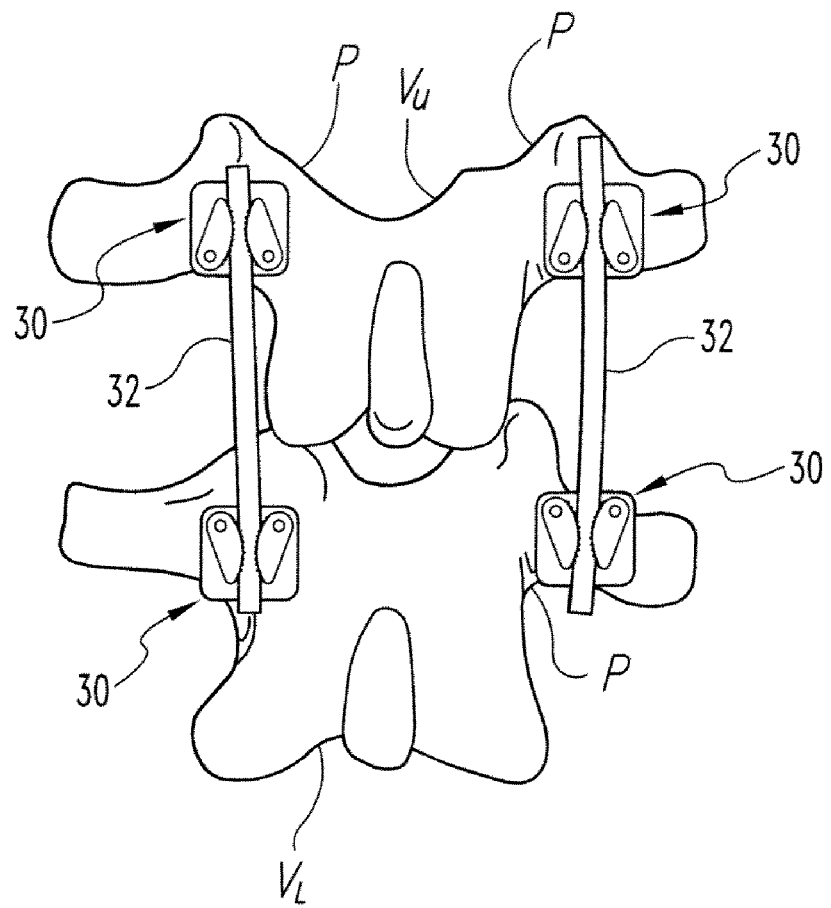
FIG. 6 is a rear elevation of the vertebrae and system shown in FIG. 5.

As shown in FIG. 4, in one embodiment a first anchor (e.g., an upper anchor $30_U$) is mounted on a first vertebra (e.g., an upper vertebra, generally designated by $V_U$), by pre-drilling the vertebra and then screwing the anchor into a pedicle P of the vertebra. A second anchor (e.g., a lower anchor $30_L$) is mounted on a second vertebra (e.g., a lower vertebra, generally designated by $V_L$) in a similar fashion. As shown in FIGS. 5 and 6, an elongate flexible member 32 is then connected to the first anchor and to the second anchor by positioning the member between the cams of the respective anchors. The elongate member 32 may then be pulled so it slides between the cams without becoming disconnected from either anchor until a desired tension is achieved in the member to induce a desired loading on the vertebrae.

In an alternative embodiment of the method, the elongate member 32 may be tensioned prior to being connected to the second anchor. In either embodiment, tension in the elongate member 32 can be readjusted to achieve precisely the desired final tension after the member is connected to the both anchors.

Additional alternative methods include positioning the anchors in different portions of the vertebrae or in different bones (e.g., a pelvis). Moreover, various components of the anchor system (i.e., the anchors and flexible member) may be altered without departing from the scope of the present invention. For instance, the anchors may include features that encourage integration with the bone. Examples of such features include providing the anchors with hollow interiors, chambers or receptacles, a porous coating or exterior surface features. In some preferred embodiments, the integration features allow bone to at least partially grow into, adhere to, attach to, resorb and/or form with the anchorage members. Elements of the system may also include bone growth material and/or bone growth facilitators, which are well known to those skilled in the art.

Figure 7:
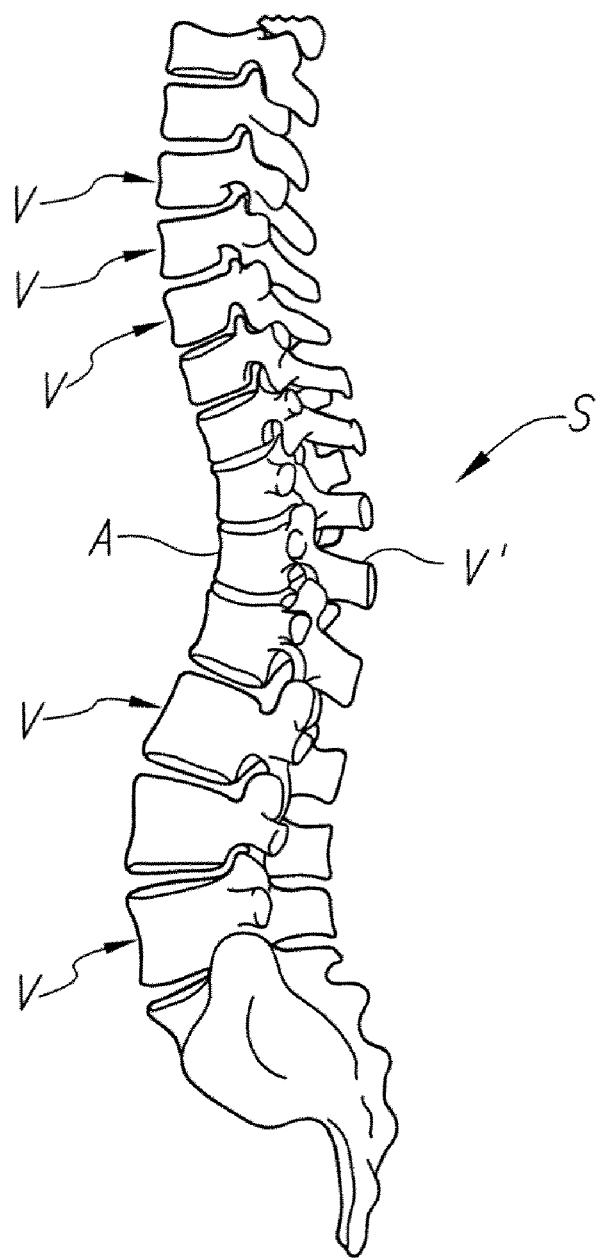
FIG. 7 is a left side elevation of a spinal column having a scoliosis deformity.
Figure 8:
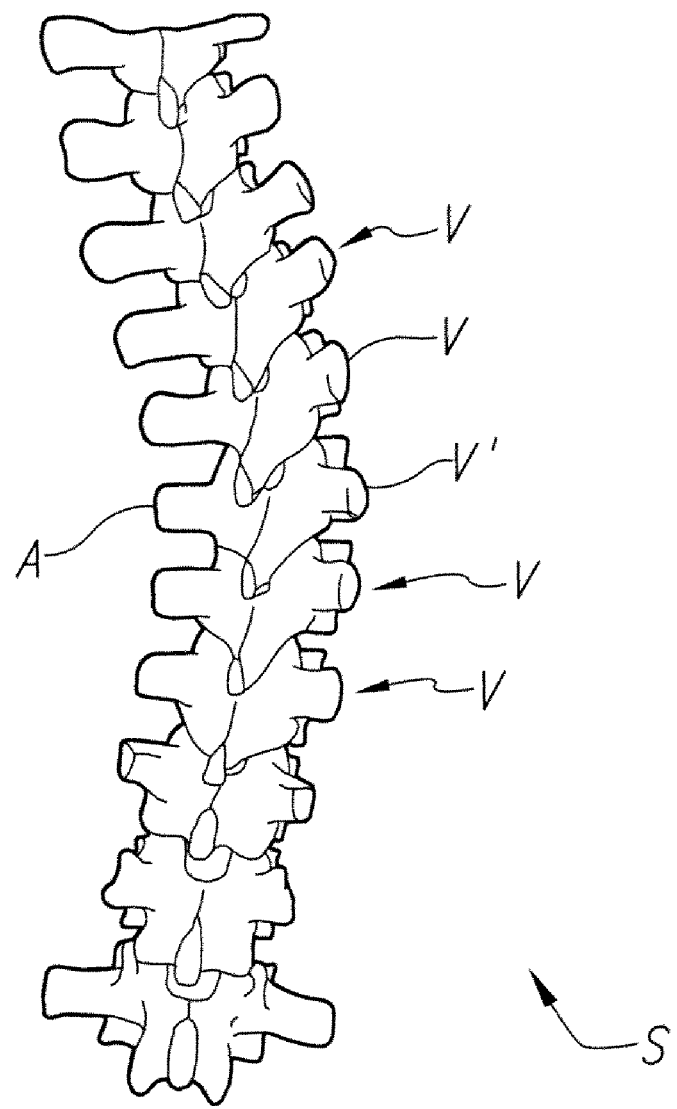
FIG. 8 is a rear elevation of the spine having the scoliosis deformity.
Figure 9:
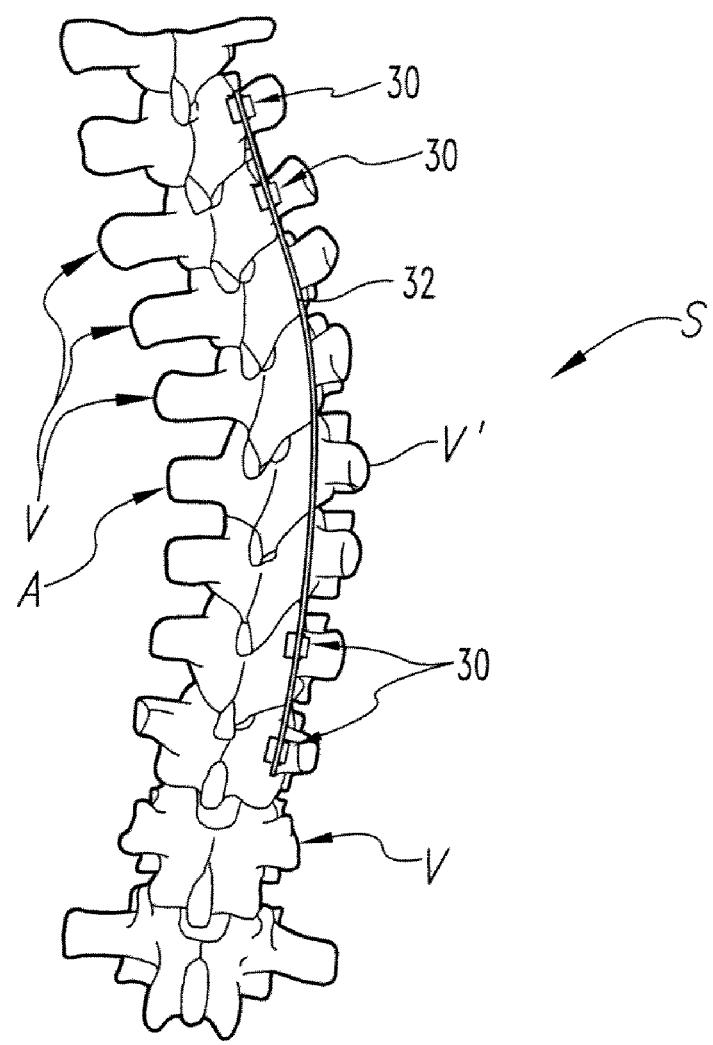
FIG. 9 is a rear elevation of the spine of FIG. 8 having a system of the present invention installed.

The systems and methods described above may be used to treat spinal column deformities such as scoliosis. FIGS. 7 and 8 illustrate a deformed spinal column, generally designated by S. The spinal column is formed from vertebrae, each generally designated by V. One vertebra V', positioned at an apparent apex of curvature A of the spinal column S is most deviated from normal. By using the systems and methods described above, a compressive load can be applied to the convex side of the spine S. It is believed that this compressive load will slow growth of the convex side. As shown in FIG. 9, anchors 30 are positioned above and below the vertebra V' at the apex of curvature A. In one embodiment, the anchors are attached to the vertebrae at the pedicles using conventional techniques known to those skilled in the art. An elongate flexible member 32 is attached to the anchors 30 and a predetermined amount of tension can be induced in the elongate member as described above. As will be appreciated by those skilled in the art, if growth occurs on the convex side of the side, the tension in the elongate flexible member 32 will increase, resulting in an increased compressive loading on the convex side of the spine S. It is believed that this increased tension will restrain further growth along the convex side of the spine S. Thus, it is believed that the systems and methods will tend to reduce curvature and/or correct the scoliosis.

As will be appreciated by those skilled in the art, a bilateral application of the systems can be used to correct a spinal deformity known as kyphosis.

It is further contemplated that more than one anchor 30 can be attached to each vertebra V, and that anchors can be attached to several vertebrae. Further, it is envisioned that the systems described herein may be used in combination with distraction systems to achieve locally desired loading on the spine S. It is also envisioned that tension can be produced in the elongate member 32 by engaging the anchors or by engaging the elongate members. For example, a distraction or compression instrument could be attached to one or more anchors to induce the desired compression in the spine and then the elongate member could be attached to the loaded anchors to maintain the applied forces. Alternatively, the elongate member could be attached to the anchorage members and then pulled to apply a load on the anchors.

Certain aspects of the present invention also have application in correction of non-spinal deformities or conditions including but no limited to joint replacement or reconstruction. In such techniques, anchors can be positioned in adjacent bony structures. An elongate flexible member can be attached to the anchors attached to the bone to maintain or apply corrective forces.

Figure 10:
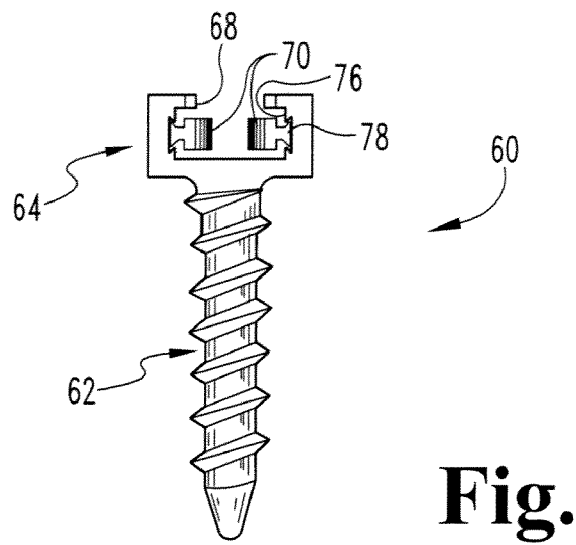
FIG. 10 is a side view of an anchor of a second embodiment of the present invention.
Figure 11:
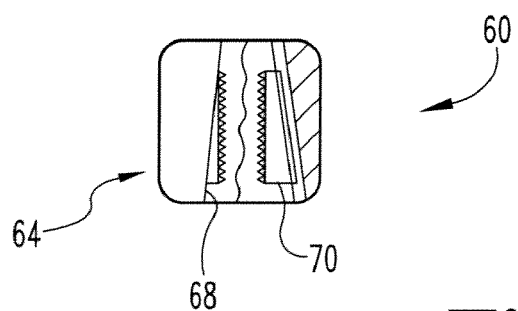
FIG. 11 is an end view in partial section of the anchor of FIG. 10.
Figure 12:
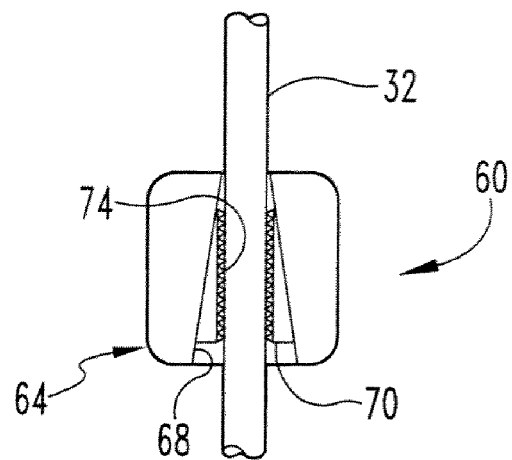
FIG. 12 is an end view of the anchor of the second embodiment having an elongate member positioned between its grippers.
Figure 13:
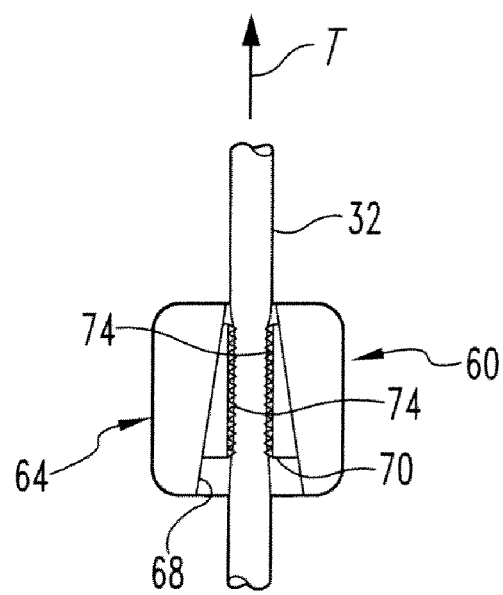
FIG. 13 is a view similar to FIG. 12 but showing the elongate member under tension so the grippers compress the elongate member.

Referring to FIG. 10, a second embodiment of an anchor of the present invention is designated in its entirety by the reference character 60. The anchor 60 includes a base, generally designated by 62, formed similarly to that of the first embodiment. Accordingly, the base will not be described in further detail. A connector, generally designated by 64, is mounted on the base 62. As shown in FIG. 11, the connector 64 has a body 66 having a tapered opening 68 having a generally rectangular cross section. A pair of wedges 70 forming a gripper are slidably received on opposite sides of the tapered opening 68 for engaging a flexible member as shown in FIG. 12. The gripper 70 is free to slide along the opening 68 between an open position as shown in FIG. 12 in which the flexible member 72 may be moved relative to the connector and a closed position as shown in FIG. 13 in which the gripper engages the flexible member so the flexible member is fixed relative to the connector. Although the wedges 70 may have other treatments without departing from the scope of the present invention, in one embodiment each of the wedges includes an inward facing serrated surface 74 for engaging the flexible member 72 received between the wedges. As shown in FIG. 10, the sides of the tapered opening 68 may include keyways 76 for engaging a keyed side 78 of the wedges 70 to capture the wedges in the opening. As will be appreciated by those skilled in the art, the anchor 70 of the second embodiment also engages the elongate member 72 tighter as the elongate member is pulled in tension away from the anchor. As other features of the anchor of the second embodiment are similar to those of the first, they will not be described in further detail.

Figure 14:
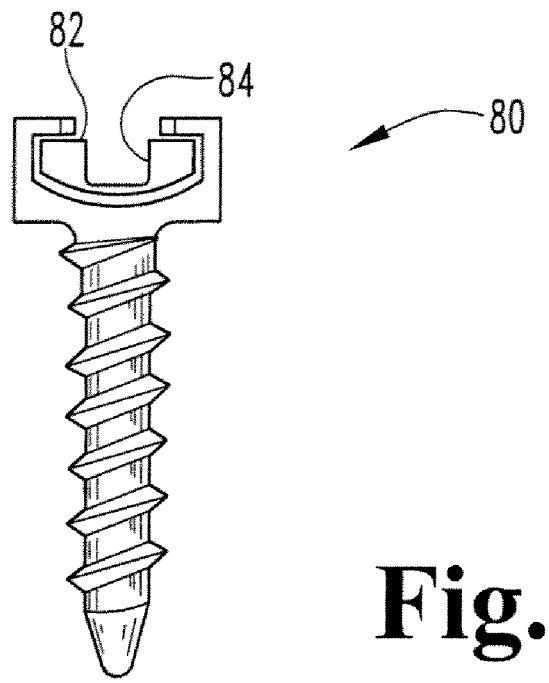
FIG. 14 is a side view of an anchor of a third embodiment of the present invention.
Figure 15:
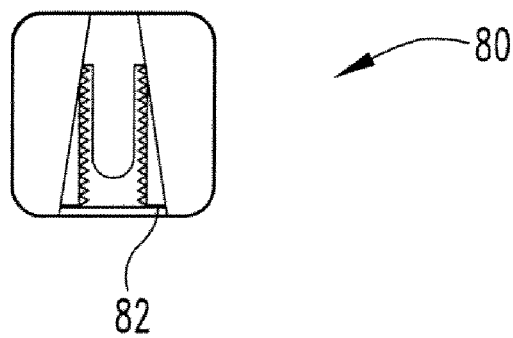
FIG. 15 is an end view of the anchor shown in FIG. 14.
Figure 16:
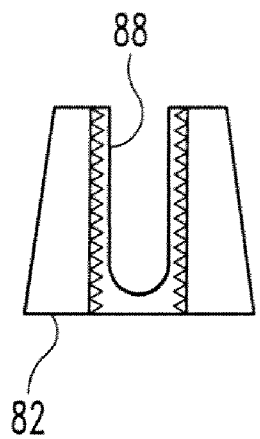
FIG. 16 is a plan view of a gripper of the anchor shown in FIG. 15.
Figure 17:
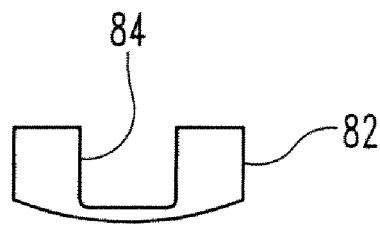
FIG. 17 is a first end elevation of the gripper of FIG. 16.
Figure 18:
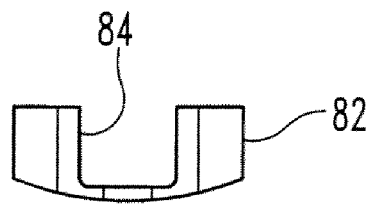
FIG. 18 is a second end elevation of the gripper of FIG. 16.

FIGS. 14 and 15 illustrate an anchor of a third embodiment of the present invention, generally designated 80. The features of the anchor 80 are similar to those of the second embodiment except that the gripper 82 is formed as a wedge having an opening 84 sized and shaped for receiving the flexible member. As further shown in FIG. 16, the gripper 82 includes a slot 88 extending longitudinally along the wedge, enabling the gripper to deform so the opening 84 moves between an open position in which the flexible member may be moved relative to the connector and a closed position in which the gripper engages the flexible member so the flexible member is fixed relative to the connector.

The anchors 30, 60, 80 and elongate flexible members 32 can be inserted using an open or a minimally invasive surgical procedure. In minimally invasive approaches employing a small incision or sleeve, such as a retractor sleeve, the spinal column can be viewed by placing an endoscope and/or a microscope (not shown) through an incision or sleeve. Techniques including imaging systems, such as fluoroscopic, radiographic, and stereotactic systems may also be employed.

An additional embodiment of the invention provides a method of treating a spinal deformity in a skeletally immature spine comprising positioning at least two anchors in at least two different vertebral bodies. The method further includes attaching an elongate member to the anchors. In accordance with this embodiment, the elongate flexible member constrains spinal growth in at least one direction thereby creating tension on the elongate flexible member and influencing the alignment of the vertebrae in the spinal column. Tensioning the elongate flexible member during surgery can also alter intervertebral alignment of the spinal column.

The anchors 30, 60, 80 may be made in whole or in part from any biocompatible material including synthetic or natural autograft, allograft or xenograft tissues, and can be resorbable or non-resorbable in nature. Additional resorbable materials include polylactide, polyglycolide, tyrosine-derived polycarbonate, polyanhydride, polyorthoester, polyphosphazene, calcium phosphate, hydroxyapatite, bioactive glass and combinations thereof. Additional non-resorbable materials include carbon-reinforced polymer composites, shape-memory alloys, titanium, titanium alloys, cobalt chrome alloys, stainless steel, ceramics and combinations thereof. Moreover, it is envisioned that the anchors may consist of one or a combination of the following elements: screw, bolt, staple, wedge, spike, spacer, cage, anchor, loop, hollow body, solid body, plate or other form. The bone engagement portion of the anchors may include threads, smooth surfaces, splines, teeth, nubs, knurling, spikes, barbs, grooves, or other conventional bone engaging treatments. Still further, the bone engagement portion of the anchors may be hollow or solid, and provided with any one or combination of fenestrations, openings, cannulations, chambers, recesses, cavities, pits, receptacles or the like to accommodate bone growth or tissue adhesion. Alternative embodiments of the anchors 30, 60 including only one cam or wedge are also envisioned and contemplated as being within the scope of the present invention.

As will be appreciated by those skilled in the art, the anchors 30, 60, 80 may be attached to various vertebral elements including a forward or rearward portion of a vertebral body, the upper or lower endplates of a vertebral body, or any of the rearward elements of the vertebral body, including the facets, pedicle, and spinous or transverse processes. The vertebral elements can also be tissue elements or ligamentous structures associated with the vertebral bodies or the spinal column. Anchor points may also include bone structures of the pelvis such as the sacrum, ilium, pubis or ichium, and may also include bone structures of the skull, shoulder structures or the ribcage.

It is envisioned that the elongate members 32 may be made from flexible cord-like or ligament-like materials and/or flexible elastic materials having appropriate material properties, shape, form, and size to induce predetermined loading across the anchors 30, 60, 80.

While the invention has been illustrated and described in detail in the drawings and foregoing description, the same is to be considered illustrative and not restrictive in character. All changes and modifications that come within the spirit of the invention are desired to be protected.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. An anchor for attaching an elongate flexible member to bone, the elongate flexible member having a central axis, said anchor comprising:
   a base adapted for attaching to bone; and
   a connector mounted on the base, the connector defining an opening extending therethrough to receive the elongate flexible member, the connector including a cam pivotably and eccentrically connected to the base by a pin and including an engagement surface facing the opening and positioned for engaging the elongate flexible member when the base is attached to bone, the cam including a cam body extending away from the pin generally parallel to the central axis of the elongate flexible member when the cam is in an open position in which the elongate flexible member may be moved within the opening relative to the connector and the cam further including serrated edges on the engagement surface of the cam body such that when the cam body is rotated around the pin toward the elongate flexible member to a closed position the serrated edges contact the elongate flexible member and restrain the elongate flexible member within the opening so the elongate flexible member is fixed relative to the connector; and wherein the base comprises an elongate longitudinal shaft having a longitudinal axis and including one or more bone anchor features adapted for anchoring to bone, the longitudinal axis of the elongate longitudinal shaft intersecting the opening in the connector that receives the elongate flexible member.

2. An anchor as set forth in claim 1 wherein the connector includes at least one pair of cams including said cam.

3. An anchor as set forth in claim 2 wherein the cams are biased toward the closed position.

4. An anchor as set forth in claim 1 wherein the cam includes a serrated surface for engaging the flexible member.

5. An anchor as set forth in claim 1 in combination with an elongate flexible member.

6. An anchor as set forth in claim 1 wherein the one or more bone anchor features comprise bone engaging threads extending along the elongate longitudinal shaft.

7. An anchor as set forth in claim 1 wherein the one or more bone anchor features comprise a porous coating on the elongate longitudinal shaft.

8. An anchor as set forth in claim 1 wherein the one or more bone anchor features comprise a bone growth promoting material that facilitates integration of the elongate longitudinal shaft with bone.

9. An anchor as set forth in claim 8 wherein the one or more bone anchor features comprise chambers defined within the elongate longitudinal shaft and with the bone growth promoting material positioned within the chambers.

10. An anchor as set forth in claim 8 wherein the one or more bone anchor features comprise a hollow interior defined within the elongate longitudinal shaft and with the bone growth promoting material positioned within the hollow interior.

11. An anchor as set forth in claim 1 wherein the elongate longitudinal shaft of the base is generally aligned with the elongate flexible member positioned within the opening of the connector.

12. An anchor as set forth in claim 1 wherein the base comprises a bone screw including a head portion and wherein the elongate longitudinal shaft comprises a threaded shank portion extending from the head portion, the cam pivotally mounted to the head portion of the bone screw by the pin.

13. An anchor as set forth in claim 12 wherein the elongate longitudinal shaft portion is centrally positioned on the head portion of the bone screw.

14. An anchor as set forth in claim 12 wherein the head portion and the threaded shank portion define a single-piece monolithic bone screw.

15. An anchor as set forth in claim 1 wherein the connector includes first and second ones of the cam arranged on opposite sides of the opening that receives the elongate flexible member, the first and second cams each pivotably and eccentrically connected to the base by a corresponding one of the pin.

16. A system for changing alignment of vertebrae of a spinal column, said system comprising:

a plurality of elongate flexible members, each of said members having a length sufficient to span at least one pair of vertebrae in the spinal column including a superior vertebra and an inferior vertebra; and a plurality of anchors, each anchor including a connector for connecting one of the plurality of elongate flexible members to a corresponding one of the anchors;

each connector defining an opening extending therethrough to receive the elongate flexible member, each connector including a cam pivotably and eccentrically connected to the base by a pin and including an engagement surface facing the opening and positioned for engaging the elongate flexible member when the base is attached to bone, the cam including a cam body extending away from the pin generally parallel to the central axis of the elongate flexible member when the cam is in an open position in which the elongate flexible member may be moved within the opening relative to the connector and the cam further including serrated edges on the engagement surface of the cam body such that when the cam body is rotated around the pin toward the elongate flexible member to a closed position the serrated edges contact the elongate flexible member and restrain the elongate flexible member within the opening so the elongate flexible member is fixed relative to the connector;

wherein the pin of a first connector is positioned on a lower portion of the connector when the connector is coupled to a superior vertebra and wherein the pin of a second connector is positioned on an upper portion of the connector when the connector is coupled to an inferior vertebra such that the first connector allows for motion of the elongate flexible member in a first direction and restricts motion of the elongate flexible member in a second direction generally opposite to the first direction and the second connector restricts motion of the elongate flexible member in the first direction and allows motion of the elongate flexible member in the second direction; and wherein the base comprises an elongate longitudinal shaft having a longitudinal axis and including one or more bone anchor features adapted for anchoring to bone, the longitudinal axis of the elongate longitudinal shaft intersecting the opening in the connector that receives the elongate flexible member.

17. An anchor for attaching an elongate flexible member to bone, comprising:

a bone anchor including a head portion and an elongate longitudinal shaft portion having a longitudinal axis and extending axially from the head portion, the shaft portion including one or more bone anchor features adapted for anchoring to bone; and a connector mounted on the head portion of the bone anchor, the connector defining an opening extending therethrough to receive the elongate flexible member, the connector including a cam pivotably mounted to the head portion of the bone anchor by a pin and including an engagement surface facing the opening and positioned for engagement with the elongate flexible member, the longitudinal axis of the shaft portion of the bone anchor intersecting the opening in the connector that receives the elongate flexible member, the cam being pivotable between an open position in which the elongate flexible member is movable within the opening relative to the connector and a closed position in which the engagement surface of the cam grasps the elongate flexible member and restrains the elongate flexible member within the opening such that the elongate flexible member is fixed relative to the connector.

18. An anchor as set forth in claim 17 wherein the engagement surface of the cam comprises a serrated surface.

19. An anchor as set forth in claim 17 wherein the one or more bone anchor features comprise bone engaging threads extending along the elongate longitudinal shaft portion of the bone anchor.

20. An anchor as set forth in claim 17 wherein the one or more bone anchor features comprise a porous coating on the elongate longitudinal shaft portion of the bone anchor.

21. An anchor as set forth in claim 17 wherein the one or more bone anchor features comprise a bone growth promoting material that facilitates integration of the elongate longitudinal shaft portion with bone.

22. An anchor as set forth in claim 21 wherein the one or more bone anchor features comprise chambers defined within the elongate longitudinal shaft portion and with the bone growth promoting material positioned within the chambers.

23. An anchor as set forth in claim 21 wherein the one or more bone anchor features comprise a hollow interior defined within the elongate longitudinal shaft portion and with the bone growth promoting material positioned within the hollow interior.

24. An anchor as set forth in claim 17 wherein the elongate longitudinal shaft portion of the bone anchor is generally aligned with the elongate flexible member positioned within the opening of the connector.

25. An anchor as set forth in claim 24 wherein the longitudinal axis of the elongate longitudinal shaft portion is generally aligned with a central axis of the elongate flexible member positioned within the opening of the connector.

26. An anchor as set forth in claim 17 wherein the bone anchor comprises a bone screw, and wherein the elongate longitudinal shaft portion comprises a threaded shank portion extending axially from the head portion, and wherein the cam is pivotally mounted to the head portion of the bone screw by the pin.

27. An anchor as set forth in claim 17 wherein the head portion and the elongate longitudinal shaft portion define a single-piece monolithic bone anchor.

28. An anchor as set forth in claim 17 wherein the elongate longitudinal shaft portion is centrally positioned on the head portion of the bone anchor.

29. An anchor as set forth in claim 17 wherein the connector includes first and second ones of the cam arranged on opposite sides of the opening that receives the elongate flexible member, the first and second cams each pivotally mounted to the head portion of the bone anchor by a corresponding one of the pin.

* * * * *